United States Patent [19]

Tessler

[11] 4,030,505

[45] June 21, 1977

[54] METHOD AND DEVICE FOR DISINTEGRATING STONES IN HUMAN DUCTS

[75] Inventor: Arthur N. Tessler, New York, N.Y.

[73] Assignee: Calculus Instruments Ltd., New York, N.Y.

[22] Filed: Nov. 28, 1975

[21] Appl. No.: 636,241

[52] U.S. Cl. ............................. 128/328; 128/24 A; 128/243
[51] Int. Cl.² ......................................... A61B 17/22
[58] Field of Search .................. 128/328, 242–244, 128/341, 345, 352, 356, 24 A

[56] References Cited

UNITED STATES PATENTS

| 872,217 | 11/1907 | Bonesteel | 128/244 X |
|---|---|---|---|
| 3,413,976 | 12/1968 | Roze | 128/328 |
| 3,735,764 | 5/1973 | Balev et al. | 128/328 |
| 3,827,437 | 8/1974 | Inaba | 128/328 |
| 3,831,585 | 8/1974 | Brondy et al. | 128/328 X |
| 3,902,499 | 9/1975 | Shene | 128/328 |

FOREIGN PATENTS OR APPLICATIONS

| 1,566,147 | 7/1970 | Germany | 128/328 |
|---|---|---|---|
| 221,209 | 10/1968 | U.S.S.R. | 128/328 |
| 123,286 | 1/1959 | U.S.S.R. | 128/328 |

*Primary Examiner*—Robert W. Michell
*Assistant Examiner*—Lee S. Cohen
*Attorney, Agent, or Firm*—David H. Semmes

[57] ABSTRACT

Method and device for disintegrating concretions, or sclerotic clots within human ducts. The method and system are particularly adapted to disintegrating stones in the ureter and kidney, as well as the bladder. The method includes axially abutting the concretion within the human duct while outwardly distending the walls of the duct adjacent the concretion, directing a series of high voltage, low amperage pulses into the ducts and discharging the pulses radially outwardly across the surface of the concretions, while flowing a liquid peripherally of the discharging pulses, so as to direct an hydroelectric impact against the concretion. The outward distending of the walls and the flowing liquid, particularly in narrow human ducts such as the ureter, prevent tissue damage by shock and burning.

10 Claims, 4 Drawing Figures

METHOD AND DEVICE FOR DISINTEGRATING STONES IN HUMAN DUCTS

CROSS-REFERENCES CROSS-RREFERENCES TO RELATED APPLICATIONS

An improvement upon METHOD AND DEVICE FOR CATHETERIZATION (Ser. No. 584,672), filed June 6, 1975 in which the present applicant was a joint inventor.

BACKGROUND OF THE INVENTION

Field of the Invention

Cystoscopy, particularly a method for removing concretions from the urinary tract, as well as placques and sclerotic clots within other human ducts. A principal difficulty in treatment within the urinary tract has been the inability of probing devices to reach the ureter or kidney. The suggested method and apparatus is of such diminutive diameter and flexibility to enable exploration and treatment in these critical areas.

DESCRIPTION OF THE PRIOR ART

West German Pat. No. 847,950
West German Pat. No. 1,218,112
West German Pat. No. 1,284,561
West German Pat. No. 2,032,501
Great Britain Pat. No. 1,082,387
Russian Pat. No. 228,865
ROZE, Pat. No. 3,413,976
BALAEV, Pat. No. 3,543,757
EDINY, Pat. No. 3,557,793
SCHMIDT-KLOIBER, Pat. No. 3,785,382
KLOZ, Pat. No. 3,792,701
POHLMAN, Pat. No. 3,823,717
ANTONEVICH, Pat. No. 3,830,240
ANTONEVICH, Pat. No. 3,861,391

Roze, (corresponding to Russian Pat. No. 228,865 and West German Pat. No. 1,218,112) employs a long medicine needle, 5 of apparent inflexibility, having an enlarged boss 6 at its end. The negative electrode 3 is in the form of an enlarged, truncated head and in turn is encircled by envelope 7 and lacquer coating 8. An inner tube 4 separates the positive electrode 5 from the head or negative electrode 3, except for the protuberant boss portion 6 of the negative electrode. Water is discharged thru electrode 5 in the form of a needle. It is submitted that this construction is of such a wide diameter and inflexibility so as to preclude exploration into the ureter and kidney.

German Pat. No. 847,950 employs sonic vibrations to crush the stone, wherein glycerin is used as a lubricant upon the concretion. German Pat. No. 1,284,561 employs a lithotrite having electrodes and a pulse generator to supply instantaneous pulsing discharges, thereby creating hydraulic shock waves in a washing liquid which has filled the bladder. It is noted that this particular technology is also correspondingly exampled in British Pat. No. 1,082,387, Russian Pat. No. 228,865 and U.S. Pat. No. 3,543,757; all in the name of Balaev. Balaev employs a system wherein electrical oscillations are converted to ultrasonoic oscillations within a fluid medium. German Pat. No. 2,032,501 teaches a vibratign longitudinal probe, together with a connection for an irrigation device. Similarly, Ediny U.S. Pat. No. 3,557,793 is an improved structure for alternately using an ultrasonic mechanical oscillation together with a controlled hydraulic impact which is produced by an electric discharge in a liquid medium surrounding the concretion.

Schmidt-Kloiber U.S. Pat. No. 3,785,382 is particular to a miniaturized mechanically oscillatory device to facilitate concretion breakdown. The patentee employs a long, thin and apparently inflexible lithotriptor guided inside a thin ureter catheter 12, allowing passage of a rinsing liquid in the annulus therebetween. The device is purely mechanical in that the electrodes 7 produce shock waves in a separate chamber maintained external to the patient's body. Similarly, Kloz U.S. Pat. No. 3,792,701 includes a transducer which is maintained externally to the patient's body, together with a vibrating probe attached to a cystoscope that includes a flushing probe.

Pohlman U.S. Pat. No. 3,823,717 teaches a particular structure for an ultrasonic probe, including a plurality of cutting teeth around a hollow tubular device to allow withdrawal of disintegrated particles. The Antonevich U.S. patents transmit ultrasonic force transversely through a catheter. The disclosure in both patents is identical; the claims of Pat. No. 3,861,391 being particular to subject matter which was divided out of the earlier Pat. No. 3,830,240. These patents suggest the use of miniaturized components so that even stones lodged high in the ureter can be fractured without the necessity of open surgery; noted as the present practice. The inventive feature of these patents comprises a wave guide to particularize the motion of a slender wire as it mechanically impacts upon the concretion, without any disclosed use of hydraulic action.

SUMMARY OF THE INVENTION

Method for removing concretions within human ducts, particularly the ureter and kidney, comprising axially abutting a concretion within a human duct, while outwardly distending the walls of the duct adjacent the concretion, generating a series of high voltage electrical pulses of sufficiently low amperage to avoid harm to human tissues; directing said pulses within an insulating medium extending to said ducts to the situs of said concretions; selectively discharging said pulses radially outwardly across the surface of said concretions; and flowing a liquid peripherally of said discharging of pulses, so as to direct an hydroelectric impact against said concretions and within the distended duct walls.

A suggested apparatus includes a narrow diameter flexible conduit of inert material extensible, for example, through the bladder and into the ureter and kidney to the situs of the concretions. The conduit may include a flexible positive electrode extending coaxially and supported in electrically insulative material. A flexible negative electrode may be peripherally embedded in the conduit apart from the positive electrode so as to present a continuous electrically conductive surface encircling and coextensive with the positive electrode at the conduit end.

A harp distender may be supported at the end of the flexible conduit, so as to extend beyond the electrodes and distend outwardly the human duct from the area of the electrodes. A liquid carrying outer annulus is supported by the flexible conduit such that liquid may be delivered simultaneously and coextensively with electrical discharges, as a hydroelectric cavitation upon the concretions. A high voltage, low amperage generating apparatus is operatively connected to the positive electrodes, such that the electrical discharges radiate from said positive electrode outwardly to said encircling negative electrode and, simultaneously, across the surface of the stone.

BRIEF DESCRIPTION OF THE DRAWINGS:

FIG. 1 there is illustrated a proposed form of the device including an outer insulating tube 10, a fluid supply annulus 12 having inlet 14 and outlet 16, a stationary hand grip 22 encircling the electrodes and a longitudinally actuable gripping element 26 encircling outer insulating tube 10. A conventional plug 24 may be utilized to activate electric wires 26, 28, extending to outer wire electrode 30 and inner wire electrode wire 32 embedded in insulated material. The end of outer wire electrode 30 is formed as a circle, such that pulses or discharges radiate from inner electrode 32. Inner insulating tube 46 provides insulation intermediate the inner electrode 32 and outer electode 30.

Figure 1:
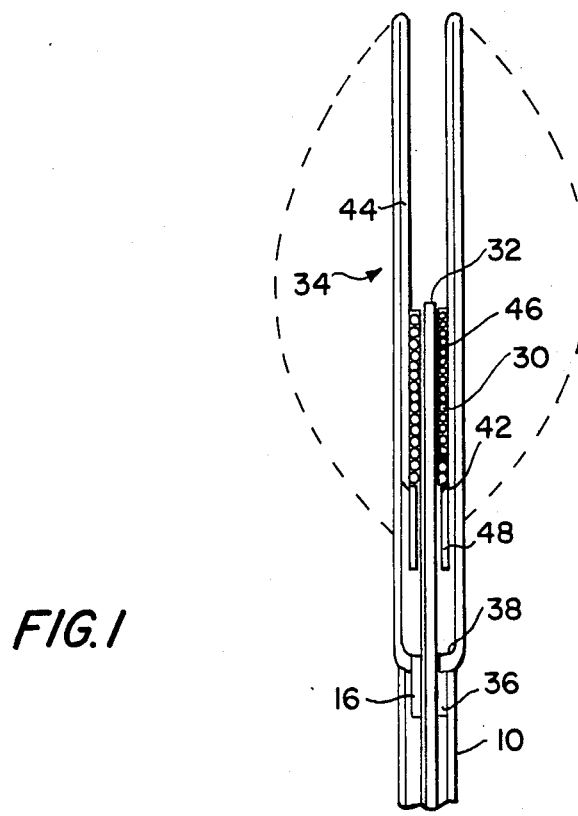
FIG. 1 is a fragmentary elevation, partially in section, showing a suggested device with the distended harp shown in phantom line.
Figure 1:
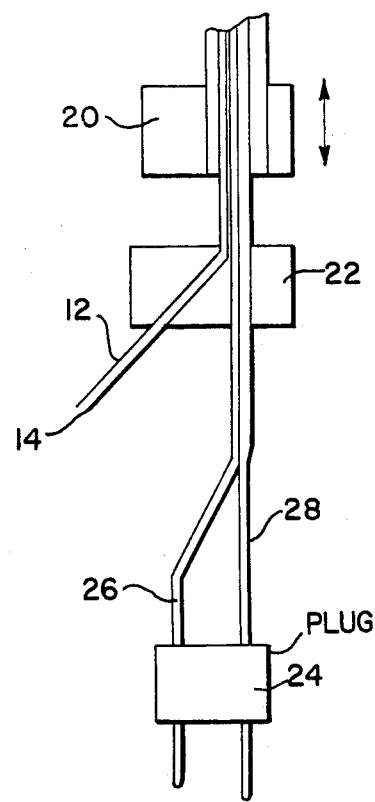

The spreading mechanism or harp exterior 34 extends from base portion 36 mounted within outer insulating tube 10, so as to define inner shoulders 38. Base portion 36 extends axially beyond the electrodes and is bent over as at 44. As will be apparent, axial movement of gripping element 20 pushes outer insulating tube axially such that the harp is distended as illustrated in phantom in FIG. 1 and as illustrated in FIG. 2 in section. In this attitude a harp 34 distends the duct walls 50 laterally outwardly of the stone 100 being attacked as at 52.

The inner portion 44 of the harp literally holds the stone in place adjacent the ends of the electrodes as the hydroelectroc cavitational effect transpires. As will be apparent, an outer insulating sheath 48 may also be provided, so as to encircle the negative outer electrode 30. Brass material such as that used in thermostats may be used to form the harp which distends the ureter and mechanically separates the wall.

Figure 2:
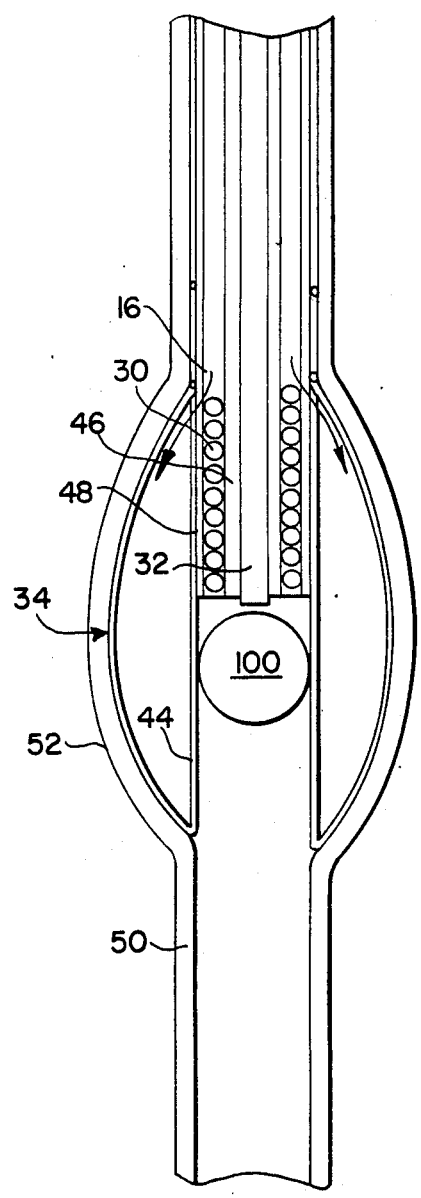
FIG. 2 is an enlarged, fragmentary sectional view, showing placement of the harp adjacent the stone so as to distend the human duct.
Figure 4:
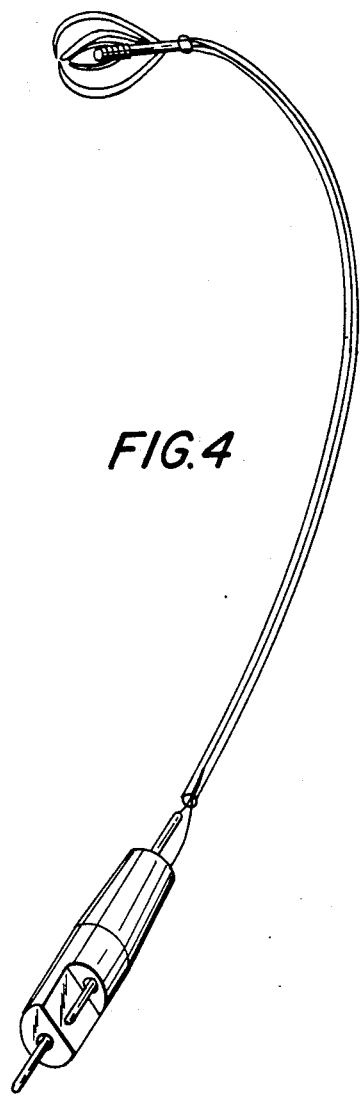
FIG. 4 is a perspective view of a device, having three brass harp distenders.

The entire device illustrated in FIGS. 1, 2 and 4 may be 1/16 inch in diameter and is adapted for use with standard cystoscopes. Since the ureter walls are closer than the bladder walls, the distension of the duct walls, eliminates burning and shock damages to the skin. This burning and shock in conventional electric discharge devices has to a large degree inhibited ureter and kidney cystoscopy.

Figure 3:
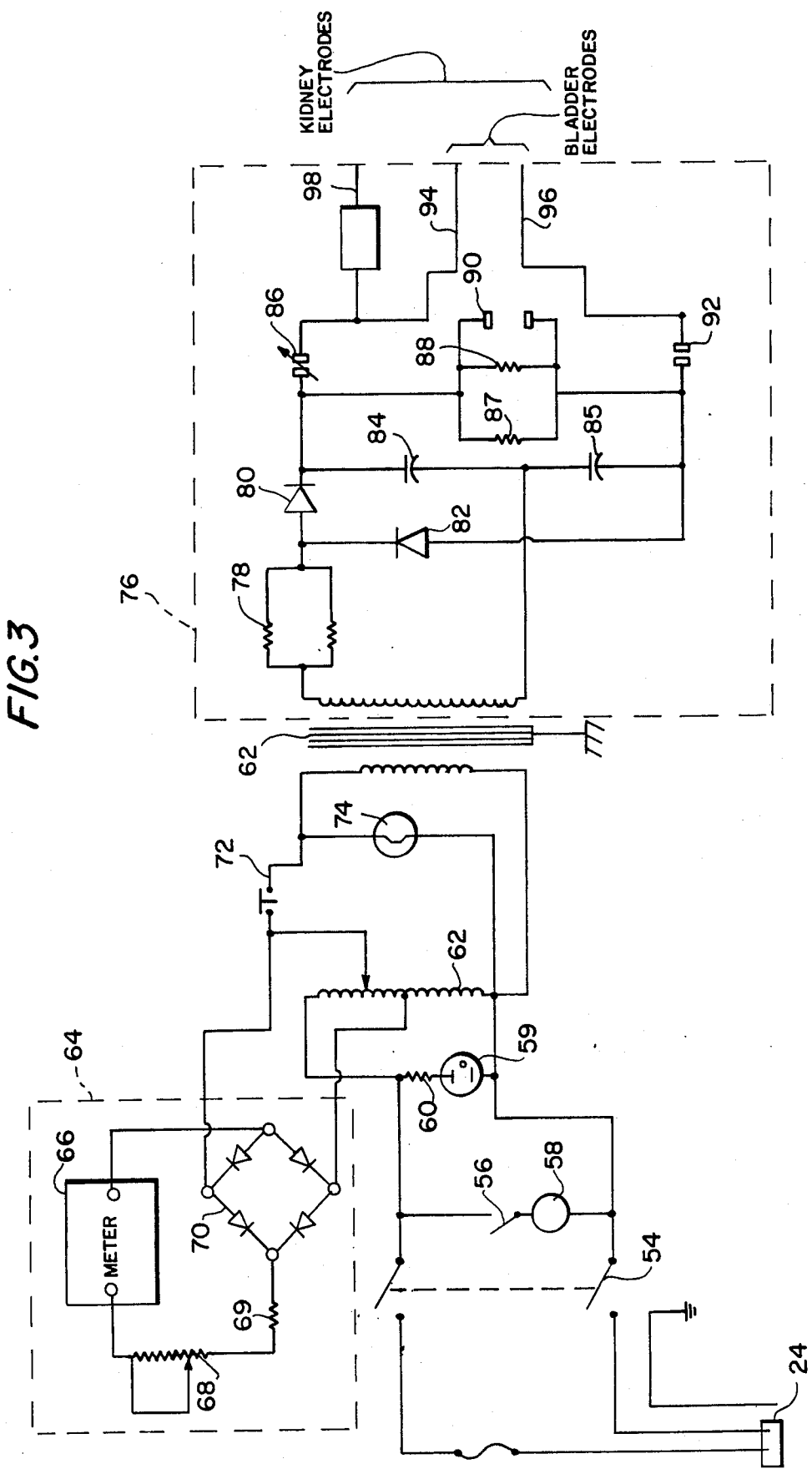
FIG. 3 is a circuit diagram of a type of circuit which may be employed.

In FIG. 3 a proposed circuit is illustrated as being powered at a conventional outlet 24 and including 3 amps slow-blow dual pole switch 54, time delay 58 and foot switch 56. A 47K ¼ W or similar resistor 60 may be employed together with a NE51H glow lamp 59. A 120 volt 2.25 amps variable transformer 62 may be employed together with time delay contact 72 and 120V incandescent lamp 74. Transformer 62 may be of the 115V-3000V 067 Amps type at 50% duty cycle, maximum. PRI leverage: 10m Amps.

The meter rectifier assembly 64 may include a 0-1 DC Milliamps meter 66, a 10K ¼W potentiometer 68, a 50K ¼W resistor 69, and Wheatstone bridge 70, including suitable 1 amp 200 PIV silicon diodes. The high voltage assembly 76 may include a pair of 25K 50W resistors 78, a pair of 1 amp 8000 PIV 11V, HC rectifiers 80–82, 0.1 mf 5000 WVDC capacitors 84, 85, a pair of 12 Meg 2W resistors 87, 88 and safety fixed spark gap 90, a variable spark gap 86 and a fixed isolation spark gap 92. A pair of bladder electrodes 94, 96 may be employed together with kidney electrode 98.

Manifestly, various types of spreading or harp mechanisms may be employed adjacent the electrodes in order to distend the duct walls and the electrode structure may be varied without departure from the spirit and scope of the invention.

I claim:

1. Method for removing concretions within human ducts comprising:
   A. axially abutting a concretion within a human duct, while outwardly distending the walls of said duct adjacent said concretion;
   B. generating a series of high voltage electrical pulses of sufficiently low amperage to avoid harm to human tissues;
   C. directing said pulses within an insulating medium extending into said duct to the situs of said concretion
   D. selectively discharging said pulses radially outwardly across the surface of said concreation; and
   E. flowing a liquid peripherally of said discharging of pulses, so as to direct an hydroelectric impact against said concretion.

2. Method for removing concretions within human ducts as in claim 1, including directing said pulses within an insulating medium extending into said duct within the ureter and kidney.

3. Method for removing concretions within human ducts as in claim 2, including discharging said electrical pulses and flowing said liquid so as to cavitate across the surface of said concretion.

4. Method for removing concretions within human ducts as in claim 3, wherein said flowing liquid is discharged at the interface of said discharging electrical pulses upon said concretion.

5. Method for removing concretions within human ducts as in claim 1, wherein said flowing liquid surges within the outwardly distended walls of said duct as an additional insulating medium.

6. A device for removing concretions within human ducts comprising:
   A. A a flexible conduit of inert material of a size to be extensible within said ducts to the situs of said concretions and having an inlet and an outlet and including:
      i. a flexible positive electrode extending coaxially within and terminating at said outlet of said conduit and being embedded in electrically insulative material; and
      ii. a negativve electrode peripherally embedded in said conduit apart from said positive electrode and terminating at said outlet of said conduit, as a continuous electrically conductive surface encircling and coextensive with said positive electrode, said negative electrode being supported apart from said positive electrode so as to define a liquid carrying outer annulus extending the length of said conduit, such that liquid may be delivered simultaneously and coextensively with an electrical discharge, as hydroelectric cavitation upon said concretions and as insulating medium intermediate said electrodes, B. a harp distender supported at said outlet of said flexible conduit and extending beyond said electrodes, means for moving said sharp distender so as to distend outwardly said ducts in the area of said electrodes; and C. a high voltage, low amperage pulse generating apparatus operatively connected to said positive electrode and said negative electrode, such that electrical discharges radiate from said positive electrode across the surface of said concretions.

7. A device for removing concretions within human ducts as in claim 6, said conduit being less than 1/16 inch in diameter.

8. A device for removing concretions within human ducts as in claim 6, said conduit being especially adapted for cystoscopy of the ureter and of sufficient length to extend into the kidney.

9. A device for removing concretions within human ducts as in claim 8, said harp distender supported at said outlet having an inner portion encircling and extending parallel beyond said electrodes and a distendable outer portion superposed with respect to said inner portion.

10. A device for removing concretions within human ducts as in claim 9, said harp distender outer portion being flexible radially outwardly of said inner portion upon longitudinal movement of said conduit of inert material, so as to distend outwardly the walls of said duct.

* * * * *